(12) United States Patent
Thys-Jacobs

(10) Patent No.: US 9,072,693 B2
(45) Date of Patent: Jul. 7, 2015

(54) MICRONUTRIENT SUPPLEMENT WITH CALCIUM, VITAMIN D OR CALCIUM AND VITAMIN D COMBINATION FOR PREMENSTRUAL/MENSTRUAL RELIEF

(76) Inventor: Susan Thys-Jacobs, Larchmont, NY (US)

( * ) Notice: Subject to any disclaimer, the term of this patent is extended or adjusted under 35 U.S.C. 154(b) by 0 days.

(21) Appl. No.: 13/439,544

(22) Filed: Apr. 4, 2012

(65) Prior Publication Data

US 2012/0195981 A1     Aug. 2, 2012

Related U.S. Application Data

(60) Continuation of application No. 12/493,559, filed on Jun. 29, 2009, now abandoned, which is a division of application No. 11/265,470, filed on Nov. 2, 2005, now abandoned.

(51) Int. Cl.
*A61K 31/593* (2006.01)
*A61K 33/10* (2006.01)
*A61K 45/06* (2006.01)
*A61K 31/59* (2006.01)
*A61K 33/06* (2006.01)

(52) U.S. Cl.
CPC .................. *A61K 33/06* (2013.01); *A61K 31/59* (2013.01); *A61K 31/593* (2013.01); *A61K 33/10* (2013.01); *A61K 45/06* (2013.01)

(58) Field of Classification Search
None
See application file for complete search history.

(56) References Cited

FOREIGN PATENT DOCUMENTS

| GB | 2169202 | * | 1/1985 | ............. A61K 33/08 |
| WO | WO94/06435 | * | 3/1994 | ............. A61K 31/56 |

OTHER PUBLICATIONS

Schneider et al., J Neural Transm, 2000; 107: 839-842.*
Stewart, J Reprod Med. 1987; 32: 435-41.*
Vieth et al., Am J Clin Nutr 2001; 73: 288-294.*
Website downloaded Jan. 11, 2013 from unc.edu/~rowlett/units/scales/clinical_data.html; 6 pages total.*

* cited by examiner

*Primary Examiner* — Christina Borgeest
(74) *Attorney, Agent, or Firm* — Gottlieb, Rackman & Reisman, PC

(57) ABSTRACT

A bolus dose supplement, foodstuff, beverage and beverage concentrate with calcium and vitamin D for the treatment and prevention of PMS, panic attacks, and postpartum depression. The combination of adequate calcium and vitamin D is provided as a multi-vitamin and mineral supplement. The bolus dose is comprised of 2 main ingredients calcium and vitamin D at 1000-1500 mg of elemental calcium in the form of carbonate or citrate or gluconate or citrate maleate and 400-20,000 I.U. of parent vitamin D.

4 Claims, No Drawings

MICRONUTRIENT SUPPLEMENT WITH CALCIUM, VITAMIN D OR CALCIUM AND VITAMIN D COMBINATION FOR PREMENSTRUAL/MENSTRUAL RELIEF

This application is a continuation of U.S. application Ser. No. 12/493,559 filed Jun. 29, 2009 now abandoned, which is a divisional of U.S. application Ser. No 11/265,470 filed Nov. 2, 2005 now abandoned.

FIELD OF THE INVENTION

This invention is directed to a micronutrient supplement in the treatment of premenstrual syndrome, postpartum depression and panic attacks. In particular, this invention relates to a multi-vitamin and mineral supplement for the relief of mood, depression, heightened anxiety, headaches, and pain symptoms.

BACKGROUND OF THE INVENTION

PMS is a very common problem that affects millions of young women during their reproductive lives, disrupting their emotional and physical well being. It is widely recognized as a recurrent, cyclical disorder related to the latter half of the menstrual cycle, subsiding with the onset of menses. The syndrome is characterized by a complex group of signs and symptoms that may include depression, mood swings, irritability, fatigue, abdominal discomfort and changes in appetite. Although many women experience only mild symptoms, as many as 30-50% suffer from troublesome symptoms. Surveys indicate that approximately 5% of North American women consider their symptoms to be severe enough to have a substantially negative impact on their health and social well being. It has been suggested that women in this latter group be defined as having Premenstrual Dysphoric Disorder (PMDD).

There is no one established therapy for PMS. A variety of treatments have been proposed over the years including lifestyle and dietary modifications, herbal remedies, hormonal therapies and pharmacologic interventions. The majority have proven ineffective or only temporizing, while other treatments have proven scientific efficacy. Some popular methods of treatment that have failed scientifically rigorous evaluation include progesterone therapy, monamine oxidase inhibitors, bromocriptine and evening primrose oil. Proven treatments of PMS include calcium supplementation, the selective serotonin receptor reuptake inhibitors (SSRIs) and the gonadotropin releasing hormone agonists. For some women, recommending lifestyle changes or a daily pharmacologic regimen is not satisfactory for a natural biological process.

Evidence has now demonstrated that PMS is associated with a calcium and vitamin D deficiency state that is clinically unmasked during the latter half of the menstrual cycle when estradiol and progesterone predominate. U.S. Pat. Nos. 4,946, 679, 5,354,743, 6,228,849 with articles Thys-Jacobs (Thys-Jacobs S, Ceccarelli S I Bierman A, Weisman H, Cohen M A, Alvir J A. Calcium Supplementaion in premenstrual syndrome. J Gen Intern Med 1989; 4:183-189; Thys-Jacobs S, Alvir M A J. Calcium regulating hormones across the menstrual cycle: evidence of a secondary hyperparathyroidism in women with PMS. J Clin Endocrinol Metab 1995; 80: 2227-2232; Thys-Jacobs S, Starkey P, Fratarcangelo P, Bernstein D, Tian J. Calcium Carbonate and the premenstrual syndrome: effects on premenstrual and menstrual symptoms. Am J Obstet Gynecol 1998;179:444-52) showed that elemental calcium and vitamin D significantly reduced PMS symptomatology. The majority of PMS symptoms such as irritability, depression, anxiety, social withdrawal, headache, and abdominal cramps are alleviated with calcium supplementation. Calcium has been demonstrated to result in a beneficial clinical response in the treatment of premenstrual symptomatology in a number of studies and has been shown to significantly benefit all 4 major categories of PMS (emotional or negative affect symptoms, bloated or water retention symptoms, food cravings and pain symptoms) reducing overall symptoms by 50%. In the largest of these clinical trials, calcium was compared to placebo. Seven hundred and twenty healthy premenopausal women between the ages of 18 and 45 years were recruited nationally in the United States and screened over 2 menstrual cycles for moderate to severe cyclically recurring symptoms. Elemental calcium, 1200 mg per day in the form of calcium carbonate effectively resulted in an overall 48% reduction in total symptom scores compared to placebo within 3 months of therapy. Daily calcium (1500 mg) and vitamin D (1600 IU) therapy as well for 3 to 4 months has also been documented to alleviate symptoms (Thys-Jacobs S, Alvir M A J. Calcium regulating hormones across the menstrual cycle: evidence of a secondary hyperparathyroidism in women with PMS. J Clin Endocrinol Metab 1995; 80: 2227-2232)

Calcium has been demonstrated in animal investigations as well as in human studies to be dynamically related to both the estrus and menstrual cycles. Fluctuations of the calcium regulating hormones (parathyroid hormone [PTH], 25 hydroxyvitamin D [25OHD], 1,25 dihydroxyvitamin D and ionized calcium) across the menstrual cycle may explain many of the features of PMS. Evidence supports cyclical changes in the calciotropic hormones in a number of investigations involving healthy premenopausal women. In 1978, Pitkin and colleagues (Pitkin R, Reynolds W A, Williams G A, Hargis G K. Calcium regulating hormones during the menstrual cycle. J Clin Endocrinol Metab 1978; 47: 626) measured calcium, the calcium regulating hormones and calcitonin across the menstrual cycle in 7 healthy premenopausal women. They were the first to report that parathyroid hormone (PTH) and the biologically active form of vitamin D-1,25 dihydroxyvitamin D progressively increased in concentration through the follicular phase of the cycle in human studies. Subsequently, both Gray et al and Tjellesen et al (Gray T K, et al. Fluctuation of serum concentration of 1,25 dihydroxyvitamin D during the menstrual cycle. Am J Obstet Gynecol. 1982; 144:880.) noted periovulatory elevations of 1,25 dihydroxyvitamin D in premenopausal women. A similar pattern of the menstrual cyclicity of the calcium-regulating hormone (total and ionized calcium, intact PTH, 1,25 dihydroxyvitamin D [1,25 (OH)2D], 25 hydroxyvitamin D [25OHD]) was noted in a study involving women with PMS compared to asymptomatic controls, with both total calcium and ionized calcium significantly varied across the three phases of the menstrual cycle (Thys-Jacobs S, Alvir M A J. Calcium regulating hormones across the menstrual cycle: evidence of a secondary hyperparathyroidism in women with PMS. J Clin Endocrinol Metab 1995; 80: 2227-2232).

Alterations in calcium homeostasis have long been associated with many affective disturbances. Hypocalcemia (abnormally low calcium concentrations) has been associated with irritability, anxiety and mania; while hypercalcemia (abnormally elevated calcium concentrations) as typified by primary hyperparathyroidism has been noted in some patients with depression. PMS shares many of the features of depression, anxiety, the dysphoric states and is remarkably similar to those symptoms associated with hypocalcemia and indeed daily calcium treatment has been found to alleviate PMS. Calcium is an essential intracellular and extracellular cation. Extracellular calcium is required to maintain normal biologic functioning of the nervous system (neuronal conductance and synaptic transmission of acetylcholine) as well as many other systems. In the brain, the synthesis of the neurotransmitters serotonin, norepinephrine and acetylcholine is dependent on intracellular calcium concentrations.

Vitamin and mineral preparations are commonly administered to treat specific medical conditions or as general nutritional supplements. Micronutrients are elements or compounds that are present in foods in small or trace amounts and include vitamins, minerals, or other elements. The macronutrients comprise carbohydrates, fats, and proteins, that supply nutrients and calories. The primary source of all nutrients is of course food. However, the majority of people do not meet the Recommended Dietary Allowance—RDA of the foods containing these essential compounds and elements. Thus vitamin and mineral supplementation has become a recognized method of meeting accepted medical and health standards.

Vitamin D is a fat soluble vitamin that is rarely found naturally in food. It is not a true vitamin, but is a steroid prohormone that is produced in the skin by ultraviolet sunlight and converted by a series of hydroxylations to a biologically active steroid hormone metabolite (M. Peacock. "Effect of calcium and vitamin D insufficiency on the skeleton. Osteoporosis Int. Suppl 8: S45-S51.(1998); Reinhold Vieth. "Vitamin D supplementation, 25-hydroxyvitamin D concentrations and safety." Am J Clin Nutrition, vol 69, pp. 842-56 (1999) (herein Peacock M; Vieth R). Vitamin D is a major regulator of calcium homeostasis and bone metabolism. However, only recently has it been hypothesized (R Vieth. "Vitamin D supplementation, 25-hydroxyvitamin D concentrations and safety." Am J Clin Nutrition, vol 69, pp. 842-56. (1999) that ingestion of adequate concentrations of vitamin D that maintain vitamin D in the sufficiency range can result in superior bone health and vitality. There have been many reported benefits of vitamin D such as in the prevention of osteomalacia, osteoporosis, breast and colon cancer, osteoarthritis progression and hypertension. Recent evidence suggests that vitamin D may have anti-inflammatory and immunosuppressive effects. In one review, (PC van de Kerkhof. "Biological activity of vitamin D analogues in the skin, with special reference to antipsoriatic mechanisms" Brit J Derm. Vol 132. pp 675-82. (1995)), active vitamin D was noted to modulate epidermal growth, keratinization and inflammation and proved effective in the treatment of the skin disease, psoriasis. Calcitriol, an active metabolite of vitamin D was noted to decrease keratinocyte proliferation, normalize keratinocyte differentiation and decrease immune activation in plaques (I Lu et al. "Modulation of epidermal differentiation, tissue inflammation, and T-lymphocyte infiltration in psoriatic plaques by topical calcitriol". J Cutaneous Pathology. Vol 23, pp 419-30. (1996)). Active vitamin D appeared to suppress immune and keratinocyte activation. Another study by Matsuyama and colleagues (W Matsuyama. "Idiopathic Hypoparathyroidism with fungal seminal inflammation. Internal Medicine." 36: 113-7; 1997) suggested that active vitamin D may possess immunological effects. Abnormalities of calcium regulation with low calcium and parathyroid hormone concentrations as described in a patient with idiopathic hypoparathyroidism resulted in fungal infections that were successfully treated with the anti-fungal treatment fluconazole only when the patient was administered active vitamin D therapy. Muller et al. reported that proliferation of T-cells and their release of cytokines such as IL-2 and interferon gamma were also suppressed by active vitamin D. (K Muller et al. "1,25dihydroxyvitamin D3 as a natural regulator of human immune functions". Journal Investigative Dermatology. Vol 1, pp. 68-71 (1996)). Vitamin D insufficiency defined as a serum 25 hydroxyvitamin D concentration below 35 ng/ml can result in reduced calcium supplies, accelerated bone turnover and suboptimal bone mass and mineralization (Peacock M.). Levels of 25 hydroxyvitamin D above 9-10 ng/ml were for many years believed to be sufficient and optimal for calcium homeostasis and bone health with the RDA (recommended dietary allowance) at 400 IU corresponding to a safe and adequate intake. Because vitamin D is lipid soluble and potentially toxic, oral intakes of vitamin D greater than 1000 IU have not been advised. One report cites that ingestion of parent vitamin D, cholecalciferol, is safe at daily doses of 2000 IU up to 10,000 IU daily with toxicity occurring at doses of 40,000 IU daily (Vieth R). Another investigation by Heaney and colleagues (Am Journal Clin Nutr 2003; 77:2040210) reported that 10,000 IU of vitamin D3 daily for 5 months was safe. Attaining a 25 hydroxyvitamin D concentration above 40 mg/ml may involve an intake of more than 2000 IU daily.

Calcium has been shown to be particularly effective in improving health. It is an essential mineral nutrient that is necessary on a daily basis for numerous key physiologic functions in the body, including nerve, muscle, skin, endocrine functions acting as an important second messenger. Deficiencies of calcium can have broad ranging adverse effects on many tissues and may manifest clinically as irritability, muscle spasm, myalgias, fatigue, anxiety and depression. Adequate dietary calcium intake has been shown to reduce bone resorption, osteoporosis and fracture risk. Chronic low dietary calcium intake results in low bone mass in many animal investigations, while calcium supplementation leads to increased bone mass (Peacock M). Calcium is required in supporting the bone formation phase of bone remodeling and is essential in bone growth, in optimizing peak bone mass and in the mineralization of the skeleton (B D Hughes. "Effect of calcium and vitamin D supplementation on Bone Mineral Density in men and women 65 years of age or older" New England Journal of Medicine. Vol 337. pp. 670-6. (1997)). Inadequate and low calcium intake can influence optimum fracture healing and probably healing in general. (T Kubo. Etal. "Osteoporosis influences the late period of fracture healing in a rat model prepared by ovariectomy and low calcium diet." Journal Steroid Biochemistry & Molecular Biology. Vol 68. pp. 197-202. (1999). "Osteoporosis influences the late period of fracture healing in a rat model prepared by ovariectomy and low calcium diet." Journal Steroid Biochemistry & Molecular Biology. 1999 Vol 68. pp. 197-202). The current DRI (Dietary Reference Intake) for adults younger than 50 years is 1000 mg of elemental calcium daily; and for adults older than 50 the DRI is 1500 mg daily of calcium.

There exists a need for a nutritional supplement that supplies appropriate and effective amounts of calcium and vitamin D at the time of symptom occurrence instead of continuous therapy for those who suffer from premenstrual syndrome, panic attacks and postpartum depression.

However, even something as natural as daily calcium and vitamin D supplementation in the treatment of PMS poses a burden to those who are resistant to a daily preventative regimen, when symptoms only occur for a few days a month. In the past few years, the concept of intermittent therapy for the treatment and management of PMS instead of continuous therapy has been studied with the selective serotonin reuptake inhibitors. Miner and colleagues in 2002 randomized women with PMS to fluoxetine bolus dosing and found that higher doses administered once or twice during the luteal phase of the cycle was effective in reducing symptomatology. This has never been shown to date for calcium and vitamin D therapy for the immediate relief of PMS symptoms.

In contrast to U.S. Pat. No. 6,228,849, which describes a method for the treatment of PMS with a daily combination of calcium and vitamin D, there exists a need for an intermittent or bolus nutritional supplement that supplies an effective amount of vitamin D and calcium at the time of immediate symptom occurrence to those who experience recurrent, though intermittent PMS symptoms, panic attacks, anxiety and depression.

SUMMARY OF THE INVENTION

This patent pertains to the micronutrient treatment of premenstrual syndrome, panic attacks and postpartum depression. An objective of this invention is to provide bolus dose supplements, foodstuffs, beverages and beverage concentrates with calcium and vitamin D in the treatment and prevention of PMS, panic attacks, postpartum depression. The combination of adequate calcium and vitamin D appears essential in mood disorders and depression. In the present invention, there is provided a multi-vitamin and mineral supplement that supplies appropriate and effective amounts of appropriate micronutrients at appropriate intervals to assure adequate intake of micronutrients needed for PMS, panic attacks and postpartum depression against nutritional losses and deficiencies.

Still further in accordance with the present invention, there is provided a multi-vitamin and mineral supplement wherein the supplement is comprised of 2 main ingredients calcium and vitamin D: at 1000-1500 mg of elemental calcium in the form of carbonate or citrate or gluconate or citrate maleate; and 400-20,000 I.U. of parent vitamin D.

These and other advantages and benefits of the invention will be apparent to those skilled in the art upon reading and understanding of the following detailed description.

DETAILED DESCRIPTION OF PREFERRED EMBODIMENTS

Many women with premenstrual symptoms desire a remedy that is effective for immediate symptom relief of anxiety, depression, headache, abdominal cramps, bloating, cravings and does not require long term, continuous daily ingestion of supplements. This method of administration (intermittent and bolus therapy with higher dosages of vitamin D) is different from the prior art that required daily, continuous therapy. It was a totally unexpected finding that proved clinically effective in many women.

This invention is directed to a multi-vitamin and mineral supplement comprised of 1000-1500 mg of elemental calcium in the form of carbonate (calcium carbonate 2500-3750 mg), citrate, gluconate or citrate maleate; 400-10,000 I.U. of vitamin D (parent vitamin D-cholecalciferol [D3] or 1000-20,000 IU of ergocalciferol [D2]). All amounts specified in the application are based on milligrams (mg); micrograms (mcg or ug) or International Units "I.U."

The multi-vitamin and mineral supplement comprises vitamin D. Vitamin D is also an essential vitamin that is included in the multi-vitamin and mineral supplement of the present invention. Vitamin D assists in the mineralization and calcification of bone, prevents rickets in children, prevents osteomalacia in adults, preserves bone and tooth growth, and lowers blood pressure. Vitamin D is fat soluble. Preferably, the multi-vitamin and mineral supplement comprises about 400-10,000 I.U. of vitamin D3 or cholecalciferol.

Vitamin D can reduce PMS symptomatology, panic attacks and postpartum depression. An adequate amount of Vitamin D should be ingested in an amount to ensure a serum 25 vitamin D concentration between 35 ng-100 ng/ml. If the serum 25 hydroxyvitamin D concentration is below 35 ng/ml, the multi-vitamin and mineral supplement preferably is comprised of about 4000-10,000 I.U. of vitamin D3 or 10,000-50,000 IU of D2. If the serum 25 hydroxyvitamin D concentration is above 35 ng/ml, the multi-vitamin and mineral supplement preferably is comprised of about 2000-6000 I.U. of vitamin D3 or 5000-10,000 of D2 in order to maintain optimal vitamin D concentrations. Preferably, in the multi-vitamin and mineral supplement, vitamin D is provided in the form of cholecalciferol at 2000 I.U. or 50 mcg (1 mcg=40 IU), to be taken on a daily basis. Preferably, in the multi-vitamin and mineral supplement, vitamin D is provided in the form of cholecalciferol at 400-10,000 I.U. (20-250 mcg) to be taken on a daily basis.

The vitamin D preferably is in the form of cholecalciferol (D3). As used herein, "vitamin D" comprises a group of, but not limited to, ergocalciferol (D2), cholecalciferol (D3), calcidiol (25 hydroxyvitamin D), or calcitriol (1,25 dihydroxyvitamin D).

Calcium, is the most important mineral in the body and is an important second messenger for numerous key cellular and enzyme functions, neuromuscular regulation and hormonal secretions, as well as for adequate bone health. It is the major bone mineral in the skeleton and is essential for optimal bone mineral acquisition. As used herein, calcium comprises elemental calcium in different forms, such as, but not limited to, calcium carbonate, calcium citrate, calcium citrate maleate, calcium gluconate, calcium lactate, calcium acetate, or calcium stearate. The total daily micronutrient supplement is comprised of about 500 to 1500 mg of elemental calcium (calcium carbonate 1250-3750 mg) daily.

The nutritional supplements of the present invention are suitably provided in any suitable dosage form known in the art. For example, the compositions are suitably incorporated into tablets, powders, granules, beads, chewable lozenges, capsules, liquids, or similar conventional dosage forms, using conventional equipment and techniques known in the art. Tablet dosage forms are preferred. Topical applications as described can also be used.

When preparing dosage forms incorporating the compositions of the present invention, the nutritional components are normally blended with conventional excipients such as binders, including gelatin, pregelatinzed starch, and the like; lubricants, such as hydrogenated vegetable oil, stearic acid and the like; diluents, such as lactose, mannose, and sucrose; disintegants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

For preparing the composition from the compounds described by this invention, inert, pharmaceutically acceptable carriers are used, which are either solid or liquid form. Solid form preparations include powders, tablets, dispersible granules, capsules, and cachets. A solid carrier is suitably one or more substances that may also act as diluents, flavoring agents, solubilizers, lubricants, suspending agents, binders or tablet disintegrating agents. The solid carrier material also includes encapsulating material. In powders, the carrier is finely divided active compounds. In the tablet, the active compound is mixed with the carrier having the necessary binding properties in suitable proportions and compacted into the shape and size desired. Suitable solid carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compounds with encapsulating material as the carrier, providing a capsule in which the active component (with or without other carriers) is surrounded by carrier, which is thus in association with it. Tablets, powders, cachets, and capsules may be used in a solid dosage form suitable for oral administration.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations that are intended to be converted, shortly before use, to liquid form preparations for either oral or parental administration. Such liquid forms include solutions, suspensions, and emulsions. These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric contained.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like as well as combinations thereof. The liquid utilized will be chosen with regard to the route of administration.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients. For convenience, the total daily dosage may be divided and administered in portions during the day if desired. Controlled and uncontrolled release formulations are also included. When administered in combination, the amounts of calcium and vitamin D thereof, may vary depending on serum concentration of some of these micronutrients and the mode of administration. For example, in one embodiment, the vitamin D is in an amount of about 2000 IU daily and the calcium is in the amount of 500 mg daily. If used in combination with vitamin D 1000, calcium 500 mg the total daily dose would be vitamin D 3000 IU, calcium 1000 mg.

The present invention is further described in the following examples. It is understood that the examples are only for illustrative purposes. The claims set forth the scope of the present invention.

EXAMPLES

The effect of the micronutrient/mineral supplement of the present invention on PMS is illustrated below.

1. Patient 1—AAK

AAK was a 35 year old premenopausal female referred for excessive fatigue, anxiety and PMS. She had a history of Hashimotos thyroiditis/hypothyroidism maintained on thyroid hormone replacement therapy and long history of recurrent PMS. Three years ago she delivered her first child and suffered severe bouts of postpartum depression for which she was prescribed an anti-depressant. Seven months ago, delivery of her $2^{nd}$ child again resulted in severe depression and excessive fatigue. Again she was offered pharmacologic intervention with an anti-depressant, but this time refused drug therapy seeking an endocrine evaluation. She claimed she resumed menses 5 months ago, and cited the worst PMS symptoms she ever had. These symptoms included extreme sadness, moodiness, heightened anxiety, nervousness, crying spells, headaches and intense cravings. She claimed she felt that emotionally she was on a roller coaster with no end in site. Laboratory evaluation revealed normal CBC, chemistries, thyroid function tests, normal sedimentation rate, normal celiac sprue antibodies. The calcium profile revealed a low 25 vitamin D at 17 ng/ml (normal range 20-54 ng/ml); intact parathyroid hormone (PTH) 68 pg/ml (normal range 10.0-65.0 pg/ml); vitamin B12—953 pg/ml. She was diagnosed with postpartum depression and PMS in the setting of severe vitamin D deficiency and secondary hyperparathyroidism. Treatment initially consisted of 1000 mg of elemental calcium (calcium carbonate 2500 mg) daily with 100,000 IU of D2-ergocalciferol weekly for one month, and then switched to daily calcium 1000 mg in combination with cholecalciferol 2000 IU. Her calcium profile corrected in 6 weeks to a serum 25 vitamin D at 57 ng/ml; Her depression and PMS markedly improved. She was instructed to maintain this daily supplemental regimen for prevention of further symptoms. Four months later she returned, complaining of recurrent PMS symptoms. She had discontinued her daily dietary nutrient regimen because she had felt so much better. Her repeat 25 vitamin D concentration was reported at 33 ng/ml. Because of her admitted noncompliance and resistance to a daily supplemental regimen, she was given a trial of intermittent bolus calcium and vitamin therapy when her symptoms recurred. An initial trial of 500 mg of calcium with vitamin D3—1000 IU at the onset of symptom occurrence proved ineffective. Steadily increasing doses of calcium and vitamin D3 resulted in a successful regimen of 1000 mg of calcium (calcium carbonate 2500 mg) with 4000 IU of vitamin D3/cholecalciferol to be taken at the time of symptom occurrence. She took this regimen as necessary for bolus dosing only, and found this to alleviate her symptoms within minutes. Her symptoms continued to return monthly, 5-7 days prior to her menstrual period and were markedly relieved with the daily bolus therapy of calcium and vitamin D.

2. Patient 2—JR.

JR was a 28 year old Caucasian, premenopausal female who presented for endocrine consultation. JR's menarche began at age 13 with regular menstrual cycles. She had a long history of incapacitating premenstrual symptoms with dysmenorrhea accompanying each menses. PMS symptoms included mood swings, intense irritability, depression and crying spells. There was no history of oligomenorrhea, eating disorders, anorexia or polycystic ovary syndrome. She did not use birth control pills, diuretics, nor was she a smoker. Past medical history was significant for lactose intolerance, irritable bowel syndrome. There was no history of celiac sprue, hypertension, diabetes mellitus or thyroid disease. Her family history was significant for one grandparent with celiac sprue. She was nulliparous. On physical examination she was a well-developed well nourished female in no acute distress. She had a normal female escutcheon pattern. BP 110/80; pulse 70. Weight 127 pounds; height 5'5". Mild facial acne vulgaris was present. The remainder of the physical examination was normal. Laboratory evaluation revealed normal CBC, chemistries, TFT's; lipid profile with triglycerides at 60 mg; ESR 1; B12-413 pg/ml; normal LH to FSH ratio 6.7 to 5.3; total testosterone normal at 28 ng; DHEAS 373; normal sprue antibodies; 25 vitamin D low at 12 ng/ml (normal range 20-54 ng/ml); with intact PTH 40.2 pg/ml (normal range 10.0-65.0 pg/ml). JR had a severe vitamin D deficiency and was prescribed elemental calcium at 1000 mg (calcium carbonate 2500 mg) with 2000 IU of cholecalciferol daily. Following 3 months of daily therapy her symptoms markedly improved and a repeat vitamin D was reported at 42 ng/ml. Seven months later, she returned for a follow up examination, citing a recurrence of her PMS symptoms. She admitted that she discontinued the daily calcium and vitamin D regimen because her symptoms had markedly improved and that she was far too 'young' to be taking tablets or any medications on a regular basis. She was very resistant to a daily treatment regimen, as her incapacitating symptoms were merely 7 days a month. Repeat 25 vitamin D level was reported at 20 ng/ml. She was initially administered a trial of intermittent, bolus calcium 500 mg (calcium carbonate 1250 mg) with vitamin D3—1000 IU for symptom occurrence relief, but without success. Incremental doses of calcium and vitamin D3 resulted in a therapeutic regimen of elemental calcium 1000 mg (calcium carbonate—2500 mg) with 5000 IU of cholecalciferol for symptom occurrence relief only. Ingestion of these tablets at the time of her PMS symptoms (moodiness, extreme fatigue, anger, bloating, and crying spells) for 7 days during the latter half of her menstrual cycle relieved her luteal symptoms.

3. Patient 3—NM

NM was a 39 year old premenopausal female referred for endocrine evaluation. NM had a significant history of Graves' disease diagnosed in 1999 complicated by bilateral orbitopathy. She subsequently underwent a subtotal thyroidectomy resulting in postsurgical hypothyroidism controlled on thyroid hormone replacement therapy. She cited recent multiple symptoms suggestive of recurrent hypothyroidism including dry skin, extensive eczema, mood swings, intense anxiety, fatigue and bloating. She claimed that over the last few years her PMS had intensified. Her menstrual cycles were regular and monthly. Past medical history was significant for Graves' disease complicated by orbitopathy. There was no history of heart disease, diabetes mellitus, asthma or liver disease. Her menarche began at age 11. She was a G2 P 1011. On physical examination she was a well-developed and nourished female in no acute distress. BP 110/70; pulse 78 . Weight 124 pounds; height 5 feet 2 inches. Skin examination revealed extensive eczema involving the upper limbs, back and anterior chest wall. The remainder of the physical examination was normal. Laboratory evaluation revealed normal CBC, chemistries and lipid profile; ESR 4; total T4-7.6 (4.5-12.0 ug/dl), TSH normal; low 25 vitamin D at 14 ng/ml (20-54 ng/ml) with an elevated intact parathyroid hormone concentration (PTH) at 66.4 pg (normal range 10.0-65.0 pg/ml). NM was biochemically euthyroid with a normal panel of thyroid function tests. She had evidence of severe vitamin D deficiency with a secondary hyperparathyroidism, and this deficiency was the most likely reason for her symptoms. She was administered ergocalciferol at 100,000 IU weekly for 4 weeks with daily calcium carbonate at 1000 mg (elemental calcium). Following one month of therapy, she was then prescribed the same daily calcium regimen of 1000 mg with 2000 IU of cholecalciferol. Four months later, a follow up appointment revealed that her PMS symptoms were no longer bothersome, and a 25 vitamin D level was reported at 45 ng/ml. Nine months later, she returned with a recurrence of her PMS symptoms (intense anxiety, fatigue, crying spells) after failing to take her daily regimen of calcium and vitamin D. A repeat 25 vitamin D level was <5 ng/ml (normal range 20-54 ng/ml). She was administered ergocalciferol—D2 at a dose of 600,000 IU over one month. Incremental trial doses of calcium and vitamin D3 resulted in an effective dose of cholecalciferol 8000 IU daily with 1500 mg of elemental calcium at the time of her PMS symptoms for the 5 days during the luteal phase of her menstrual cycle. She agreed to take the intermittent dosing regimen with the higher, but shorter course of therapy that significantly alleviated her symptoms.

4. Patient 4—KV

KV was a 27-year-old Caucasian female referred for endocrine evaluation. KV's menarche began at age 13 with regular cycles. There was no history or PCOs, although there was a history of bilateral ovarian cysts. She had a 14 year history of moderate/severe PMS manifested by panic attacks, moodiness, anger, crying spells, frequent headaches, menstrual cramping and heightened irritability. Acne vulgaris had become a problem over the last year and half. Past medical history was significant for lactose intolerance and a history of delayed healing of a metatarsal fracture in 2003. There was no history of diabetes mellitus, hypertension, thyroid disease or celiac sprue. She was a G0 P0. On physical examination she was a well-developed and well nourished female no acute distress. BP 110/70; pulse 78. Weight 106 pounds; height 5 feet 3 inches. She had a normal female escutcheon pattern. There was no evidence of acanthosis nigricans or a dorsal hump. Skin examination revealed acne vulgaris eruptions on the face, back and anterior chest wall. The thyroid gland was normal in size and the remainder of the physical examination was normal. Laboratory evaluation revealed normal CBC and chemistries; normal thyroid function tests; B12—388 pg/ml; serum insulin normal at 4.6; DHEAS normal at 408 ug; total testosterone normal at 23 ng; negative celiac sprue antibodies; 25 hydroxyvitamin D low at 18 ng/ml (20-54 ng/ml); intact PTH 16.2 pg (normal range 10.0-65.0 pg/ml); 24 hour urine calcium excretion 192 mg. KV had a severe vitamin D deficiency. She was provided ergocalciferol at 150,000 IU weekly for 4 weeks with daily calcium at 1500 mg (calcium carbonate 3750 mg) daily. Following 4 weeks, she was switched to cholecalciferol 2000 IU with calcium 1500 mg daily. Her symptoms were markedly improved and her panic attacks resolved. A repeat 25 hydroxyvitamin D level at 3 months was reported at 50 ng/ml. One year later, she returned complaining of the worst PMS and panic attacks she had ever experienced. A repeat 25 hydroxyvitamin D was reported at 20 ng and deficient. She claimed that she had discontinued the daily calcium and vitamin D regimen because her symptoms had markedly improved. She was very resistant to a daily treatment regimen as she only experienced symptoms for a few days each month. She was prescribed a trial of cholecalciferol 4000 IU daily with calcium 1000 mg daily on those days she was symptomatic (10 days) with marked improvement of her PMS and panic attack symptoms.

5. Patient 5.—TT

TT was a 36-year-old premenopausal female referred for endocrine evaluation. TT had a long 16 year history of PMS manifested by mood swings, fatigue, irritability, severe tension and depression. At some point she had been prescribed an antidepressant with minimal relief of premenstrual symptoms. She now cited that she was currently five months postpartum from her second pregnancy, was actively breastfeeding and experiencing hormonal changes very similar to her previous severe, debilitating PMS. She had been recently labeled by both her gynecologist and a psychiatrist as suffering with postpartum depression and was now seeking a second opinion. TT was very concerned that she had an endocrine problem that might be contributing to her current symptoms and not a psychiatric disturbance. Besides PMS, TT had a significant history of oligomenorrhea, bilateral ovarian cysts, severe hyperemesis of pregnancy twice and cholestasis of pregnancy. Past medical history was not significant for polycystic ovary syndrome, thyroid disease, hypertension, diabetes mellitus, or asthma. She entered menarche at age 12 with a long history of oligomenorrhea. She was a G3 P 2012.

On physical examination she was a well-developed well nourished female in no acute distress. Weight 131 pounds; height 5 feet 3½". BP110/70; pulse 60. The remainder of the physical examination was normal. Laboratory evaluation revealed normal CBC, chemistries, thyroid function tests; serum insulin normal at 4.2; DHEAS—174 ug; E2<32 pg; 25 vitamin D—low at 11 ng/ml (normal range 20-54 ng/ml) with elevated intact PTH 55.6 pg and 24 hour urine calcium low at 89 mg. TT had evidence of a calcium dysregulation with a vitamin D insufficiency and elevated parathyroid hormone concentration, which is usually seen in the PMS sufferer. TT's presentation, while atypical feature for PMS (as she was breastfeeding and not menstruating yet), is a very common presentation in a postpartum woman with depression. TT was prescribed ergocalciferol 100,000 IU weekly for one month with calcium 1500 mg daily, and then switched to cholecalciferol 2000 IU daily with 1500 mg of elemental calcium (calcium carbonate 3750 mg). Her symptoms of depression, fatigue, cravings, headaches and anxiety markedly improved and a repeat 25 vitamin D level was reported at 45 ng/ml. Six months later, she returned for a follow up visit having discontinued breastfeeding. Her menses had resumed normally. She had also discontinued the daily calcium and vitamin D therapy and admitted to a recurrence of severe PMS symptoms. A repeat 25 hydroxyvtiamin D was 35 ng. An initial trial of 500 mg of elemental calcium (1250 mg calcium carbonate) with vitamin D3—1000 IU failed to adequately relieve her PMS symptoms. Cholecalciferol 2000 IU with calcium 1000 mg proved a bit more effective, but a trial of vitamin D3-cholecalciferol at 8000 IU with 1000 mg elemental calcium in the form of carbonate proved to be the most efficacious in the alleviation of her symptoms 6. Patient 6.—JRR JRR was a 52 year old male who referred himself for endocrine evaluation of possible PMS. He had read about PMS and was convinced that he too, suffered from this disorder. His 5 daughters all had PMS before their menstrual periods. He claimed that most of the year, he was basically a happy guy, content with his job, family and life. However, every autumn and well into the winter his family noted that he became depressed, very moody, cranky and often anxious about things that normally wouldn't bother him. He complained of lack of energy, diffuse muscle aches, sleep difficulties, sense of hopelessness and diminished libido. His family teased him that he had PMS during those months. His primary care physician prescribed an antidepressant with some limited relief of his symptoms. However, he was concerned that a hormonal problem existed and discontinued the antidepressant. Past medical history was not significant for cardiac disease, hepatitis, thyroid disease, hypertension, diabetes mellitus, or asthma. He had a long history of lactose intolerance. On physical examination he was a well-developed well nourished male in no acute distress. Weight 220 pounds; height 6 feet 4½". BP130/70; pulse 68. The remainder of the physical examination was normal. Laboratory evaluation revealed normal CBC, chemistries, and thyroid function tests; B12—normal at 630 pg; total testosterone normal at 460 ng; celiac sprue antibodies were negative; 25 vitamin D—low at 9 ng/ml (normal range 20-54 ng/ml) with elevated intact PTH (parathyroid hormone) 75.2 pg and 24 hour urine calcium low at 50 mg. JRR had a severe vitamin D deficiency with a secondary parathyroidism—evidence of a calcium dysregulation. He was told that he did not have PMS, which is defined as a menstrual luteal phase disorder, as he was not a menstruating female, but did have a severe vitamin and mineral deficiency in association with depression. He was prescribed ergocalciferol—D2—150,000 IU weekly for 4 weeks in combination with elemental calcium 1000 mg (in the form of calcium carbonate 2500 mg). Four weeks later, JRR claimed he felt dramatically better. A repeat 25 hydroxyvitamin D concentration was reported at 52 ng/ml with normal intact PTH. He was maintained on calcium 1000 mg with vitamin D3-cholecalciferol 2000 IU. Nine months later, JRR returned with similar complaints, admitting that he had discontinued the calcium and vitamin D3 therapy 5 months ago, because he had felt much better. He had restarted the calcium and vitamin D3 therapy one week ago, but was still very depressed, tired and not feeling well. He refused a course of antidepressants. Because of his yearly and recurrent affective complaints, he wanted an effective, intermittent remedy that he could easily administer. He was resistant to a daily maintenance treatment, when he felt just fine most of the year. A repeat 25 hydroxyvitamin D level was reported at 30 ng/ml. He was prescribed bolus calcium and vitamin D3 therapy with 1000 mg of calcium and vitamin D3—8000 IU daily, which proved to be a successful therapy for him and which he continued to take seasonally.

While various embodiments of a multi-vitamin and mineral supplement have been disclosed, it should be understood that modifications and adaptations thereof will occur to one skilled in the art. Other features and aspects of this invention will be appreciated by those skilled in the art upon reading and comprehending this disclosure. Such features, aspects, and expected variations and modifications of the reported results and examples are clearly within the scope of the invention.

What is claimed is:

1. A method of treating premenstrual/menstrual syndrome comprising a per day bolus combination supplement of vitamin D and calcium administered during the presence of symptoms, whereby the resulting 25 hydroxyvitamin D level is achieved and maintained at, between, about 35-100 ng/ml, wherein the calcium is 1000-1500 mg of elemental calcium in the form of a carbonate, citrate, gluconate or citrate maleate and the vitamin D is 5000-10,000 I.U. of parent vitamin D3 (cholecalciferol) or vitamin D2 (ergocalciferol).

2. A method of treating premenstrual/menstrual syndrome comprising a per day bolus combination supplement of vitamin D and calcium administered during the presence of symptoms, whereby the resulting 25 hydroxyvitamin D level is achieved and maintained at, between, about 35-100 ng/ml, wherein the calcium is 1000-1500 mg of elemental calcium in the form of a carbonate, citrate, gluconate or citrate maleate, and the vitamin D is vitamin D3 in a dose of 5000-10,000 I.U. at the time of symptom occurrence for 5-10 days or vitamin D3 in a dose of 10,000-50,000 I.U. for 5 days at the time of symptom occurrence.

3. A method of treating premenstrual/menstrual syndrome comprising a per day bolus combination supplement of vitamin D and calcium administered during the presence of symptoms, whereby the resulting 25 hydroxyvitamin D level is achieved and maintained at, between, about 35-100 ng/ml wherein the supplement comprises between 5,000-10,000 I.U. of parent vitamin D3 or D2 per day for 10 days administered at the time of symptom occurrence.

4. A method of treating premenstrual/menstrual syndrome comprising a per day bolus combination supplement of vitamin D and calcium administered during the presence of symptoms wherein the supplement comprises between 10,000 to 50,000 IU of parent D3 or D2 per day for 5 days administered at the time of symptom occurrence for a patient with a serum concentration of 25 hydroxyvitamin D below 35 ng/ml.

\* \* \* \* \*